United States Patent [19]

Thiem et al.

[11] 4,112,005
[45] Sep. 5, 1978

[54] PROCESS FOR THE PREPARATION OF MONONITRO-AROMATIC COMPOUNDS

[75] Inventors: Karl-Werner Thiem, Cologne; Adolf Hamers; Josef Heinen, both of Leverkusen, all of Germany

[73] Assignee: Bayer Aktiengesellschaft, Leverkusen, Germany

[21] Appl. No.: 795,249

[22] Filed: May 9, 1977

[30] Foreign Application Priority Data

May 19, 1976 [DE] Fed. Rep. of Germany ....... 2622313

[51] Int. Cl.$^2$ .................... C07C 79/10; C07C 79/12
[52] U.S. Cl. ................ 260/645; 260/558 P; 260/612 D; 260/646; 568/706
[58] Field of Search ........... 260/558 P, 612 D, 621 N, 260/645, 646

[56] References Cited

U.S. PATENT DOCUMENTS 3,836,601  9/1974  Frey et al. ............................ 260/645

Primary Examiner—Leland A. Sebastian
Attorney, Agent, or Firm—Burgess, Dinklage & Sprung

[57] ABSTRACT

The present invention relates to an improved continuous process for the preparation of mononitro-aromatic compounds which comprises (1) nitrating a reactive aromatic compound in the absence of sulphuric acid until mono-nitration is essentially complete, said nitration being carried out in 40 to 68% strength by weight nitric acid, (2) separating mechanically the nitration reaction mixture into an inorganic phase and an organic phase, (3) washing of the organic phase with water and dilute alkali solution and subsequent separation of the unconverted starting material end of the adhering water by means of rectification (4) feeding the inorganic phase and, if necessary, the wash water of the first water wash of the organic phase, to a rectification column in which (a) water is withdrawn over the top (b) optionally a fraction which has a lower nitric acid content than the feed is withdrawn from a sidestream takeoff in the rectifying section of the column and (c) a fraction which has a higher nitric acid content than the feed is taken off from the sump, (5) recycling said material withdrawn from the sump of the column to the nitration reaction vessel with the addition of fresh concentrated nitric acid and (6) withdrawing from the system an amount of the top product from the column which corresponds to the water of reaction and that which enters with the nitric acid that is added.

16 Claims, 7 Drawing Figures

PROCESS FOR THE PREPARATION OF MONONITRO-AROMATIC COMPOUNDS

BACKGROUND OF THE INVENTION

The present invention relates to an improved continuous process for the preparation of mononitro-aromatic compounds by nitrating aromatic compounds by means of aqueous nitric acid without the use of sulphuric acid.

Most nitrations of aromatic compounds are carried out in a mixture of nitric acid and sulphuric acid, the nitric acid being employed only in a small molar excess.

A known process for the preparation of mono-, di- and tri-nitrotoluene is the so-called Schmid-Meissner process (Chem. Eng. 9, 161 (1966)), in which the mixed acid nitration and working up are carried out in a continuous process. With this process, the sulphuric acid, which is diluted by the water of reaction and in some cases by water which has been additionally added, must be re-concentrated before it is reused and this requires high temperatures. A number of technical, economic and ecological problems result from this.

The nitration of aromatic compounds with nitric acid on its own in general requires a molar excess of acid relative to the aromatic compounds employed, since the concentration of nitronium ions in pure nitric acid is lower than that in mixed acid.

The water of reaction formed during the nitration leads to dilution of the nitric acid, so that the nitration cycle cannot be repeated an arbitrary number of times re-using the nitric acid which has already been employed for nitration since, as the dilution increases, the rate of the nitration reaction decreases to an ever greater extent. A process of this type can therefore not be used for continuous operation of the reaction, prerequisites for which are constant reaction conditions and above all a constant rate of reaction.

In order to ensure economical operation of the process, it was necessary to develop a process for removing the water of reaction.

Thus, a process in which the nitration is carried out in a distillation column is described in Ind. Eng. Chem. 34, 286 (1942) and 36, 447 (1944). In this case, the unreacted hydrocarbon passes over the top of the column as a water/aromatic compound mixture which boils as an azeotrope.

After separating off the water, the aromatic compound is fed back to the column as reflux. The sump product (nitro-aromatic compound and nitric acid) is separated in a second column.

Furthermore, a process for the nitration of benzene, toluene and xylene in which the nitration is carried out in excess aqueous nitric acid at 100° to 120° C is described in U.S. Patent Specification No. 2,739,174. By withdrawing the reaction mixture below the reaction zone, a hydrocarbon-free mixture of water, nitric acid and the nitro-aromatic compound is obtained and this is fed as such to a distillation stage. An azeotropic mixture of water and the nitro-aromatic compound is taken off over the top and is separated after cooling. The nitric acid collects in the sump of the column and is removed from there.

Rectification is incomplete with both processes, as described on page 3 of German Offenlegungsschrift (German Published Specification No.) 2,240,048, and this manifests itself in the relatively low yields. With this process it is possible to achieve an increase in the yield only with high expenditure on technical measures. Moreover, with both processes distillation of the reaction mixture involves greater exposure to heat and thus give rise to hazards from the safety point of view (compare Chem. Eng. 9, 163 (1966)).

Furthermore, a process for the preparation of 1-nitronaphthalene by nitration of naphthalene in at most 30% strength by weight nitric acid is known from German Patent Specification No. 558,468; in this process the nitric acid which remains after the nitration product has been separated off is restored to its original content with fresh concentrated nitric acid and re-used. According to the data given in this patent specification, the reaction proceeds too violently and leads to the formation of undesired by-products when the concentration is higher than 30% by weight. The disadvantage of this process is, on the one hand, that the reaction times are long (8 hours), which makes the use of continuously operating reactors uneconomical, and, on the other hand, that the reaction volume continuously increases as fresh concentrated nitric acid is added and this stands in the way of economical cycling of the nitric acid.

With the process described in German Offenlegungsschrift (German Published Specification) No. 2,240,048 for the nitration of aromatic hydrocarbons with aqueous nitric acid, the aromatic hydrocarbon is allowed to bubble, in the vapour state, through aqueous nitric acid.

In this case, the water of reaction which is formed goes into the vapour phase as a hetero-azeotrope with the unconverted aromatic hydrocarbon and is withdrawn from the system after condensation of the azeotrope and phase separation of the organic phase.

The process has the disadvantage that relatively large amounts of the aromatic compound are fed in the cycle and the energy costs are thus necessarily higher than when the aromatic compound is largely or completely converted. Since the reaction can proceed only at the boundary layer between the gaseous and the liquid phases, the space/time yield is, moreover, smaller than in the case of a reaction which proceeds in the liquid phase.

Furthermore, a process for the nitration of halogenated benzene derivatives in which the hydrocarbon is reacted in the vapour phase with nitric acid in the presence of a solid inorganic oxide as the catalyst is described in German Offenlegungsschrift (German Published Specification) No. 2,510,095. Disadvantages of this process are the catalyst necessary for the reaction and the fact that the space/time yield is lower than that for a reaction carried out in the condensed phase.

The nitration of aromatic hydrocarbons which is described in German Offenlegungsschrift (German Published Specification) No. 2,249,373 is also subject to the same disadvantage, that is to say the necessity for a catalyst (perfluoroalkanesulphonic acids).

In another process (German Offenlegungsschrift (German Published Specification) No. 2,220,377) the nitration of anthraquinone is carried out in excess nitric acid. In this case, the nitric acid content of the reaciton mixture is higher than that of the azeotropic mixture after the nitration has ended. The reaction mixture is subsequently separated into the nitration product and two nitric acid fractions (acid content > 70% by weight) of different concentrations and of these the more concentrated fraction is re-used for the nitration and the more dilute fraction serves to regulate the rate of reaction. However, this process has the disadvantage that the water of reaction cannot be withdrawn from the system as water but only in the form of dilute nitric acid and this leads to losses of nitric acid. Furthermore, aromatic compounds which are nitrated easily cannot be nitrated by this process since the reaction frequently proceeds too vigorously and in an uncontrolled manner.

DESCRIPTION OF THE INVENTION

The object of the invention is to develop a fully continuous, reliable and economical process for the mononitration of reactive aromatic compounds with economical cycling of the excess nitric acid without the use of sulphuric acid or other catalysts.

According to the invention, this object has been achieved by carrying out the nitration in 40 to 68% strength by weight nitric acid, separating the reaction mixture, if appropriate after dilution and/or lowering the temperature, by mechanical means into an inorganic phase and an organic phase and feeding part or all of the inorganic phase to a rectification column in which water is withdrawn over the top and, optionally, a fraction which has a lower nitric acid content than the feed is withdrawn from a sidestream take-off in the rectifying section of the column and a fraction which has a higher nitric acid content than the feed is taken off from the sump, and by recycling the material withdrawn from the sump of the column, optionally together with the remainder of the inorganic phase, to the nitration and withdrawing from the system an amount of the top product from the column which corresponds to the water of reaction.

The process according to the invention is suitable for the preparation of optionally substituted mononuclear and polynuclear aromatic hydrocarbons of the benzene, naphthalene, anthracene, phenanthrene, diphenyl or diphenyl ether series.

Preferably, those mononuclear and polynuclear aromatic hydrocarbons which are substituted by one or more alkyl and/or cycloalkyl and/or alkoxy and/or hydroxyl and/or acylated amino groups and/or halogens are employed.

Examples of possible alkyl and cycloalkyl radicals are hydrocarbons with up to 6 C atoms, such as methyl, ethyl, n-propyl, iso-propyl, n-butyl, iso-butyl, tert.-butyl, n-pentyl, 2-methylpentyl, 3-methylpentyl, n-hexyl, cyclopentyl and cyclohexyl. Suitable alkoxy radicals are those with up to 5 C atoms, such as methoxy, ethoxy and propoxy. Possible acylated amino groups are those with up to 8 C atoms and the acyl radicals are, for example, acetyl or benzoyl groups. Halogens which may be mentioned are fluorine, chlorine, bromine and iodine.

Preferred compounds are, for example, the following aromatic hydrocarbons: benzene, naphthalene, o-, m- and p-xylene, toluene, 1,3,5-triisopropylbenzene, ethylbenzene, propylbenzene, isopropylbenzene, 1-methylnaphthalene, chlorobenzene, chloromethylbenzene, chloroethylbenzene, biphenyl and diphenyl ether.

Compounds which are particularly suitable for the process are, for example, benzene, toluene, xylene and naphthalene.

The process according to the invention can be carried out in the temperature range from about 30° to about 120° C and preferably from about 50° to about 90° C and it is possible to work under normal pressure, elevated pressure or reduced pressure.

The nitration can be carried out in excess aqueous nitric acid using concentrations of 40 to 68% by weight of $HNO_3$ and preferably using concentrations of 45 to 67% by weight of $HNO_3$ and the molar ratios of nitric acid, calculated as $HNO_3$, to the aromatic compound can be in the range of about 4 : 1 to about 50 : 1 and preferably in the range of about 7 : 1 to about 30 : 1.

Here and in the text which follows, the molar ratio is understood as the ratio of mols of $HNO_3$ which are contained in the aqueous nitric acid ($NHD_3 + H_2O$) to the mols of aromatic compounds employed.

The nitration is advantageously carried out until the conversion of the starting material is such that only very small amounts of undesirable secondary products are formed in addition to the desired mononitro product. This is generally the case with conversions of 90 to 98%.

The individual process steps of the process according to the invention, which are shown in the accompanying drawings in which.

In these FIGS..

A denotes equipment for carrying out nitration reactions (nitration reactor),
B denotes equipment for mixing and diluting,
C denotes a mechanical separating device for separating the organic phase from the inorganic phase,
D denotes equipment for rectifying the inorganic phase,
E denotes equipment for washing or extrcting the organic phase with water or aqueous alkaline solutions,
F denotes equipment for extracting an inorganic phase through an organic phase and
G denotes equipment for rectifying the organic phase a. Preparation of the nitrating acid (compare FIG. 1).

Figure 1:
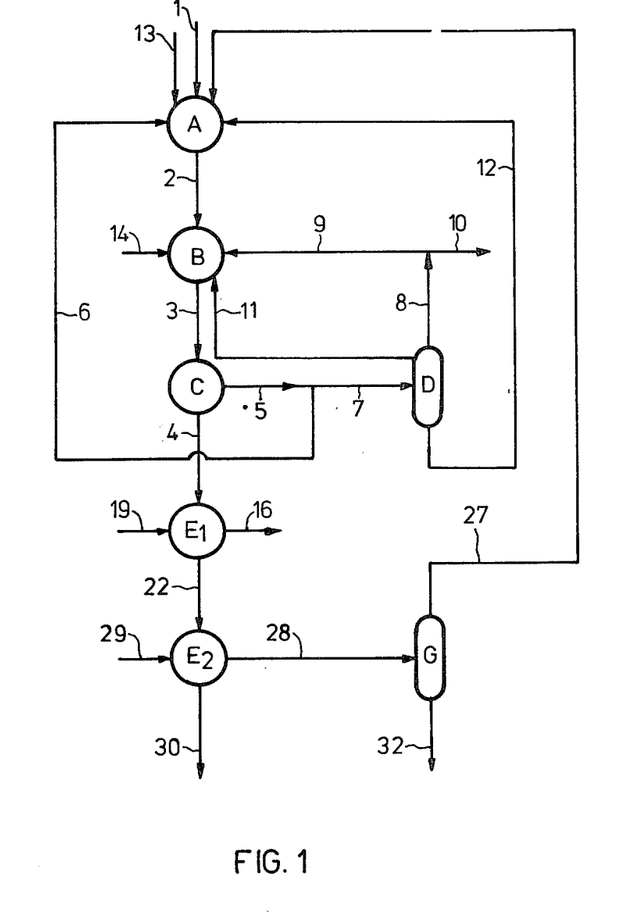
FIGS. 1 to 7 are block diagrams of different embodiments of the invention which are described in the text which follows. The numbering of the substance streams is also indicated in the block diagrams.

The nitric acid to be employed in the nitration is mixed from azeotrope nitric acid (stream 12), the inorganic phase obtained after the phase separation (stream 6) and fresh nitric acid (stream 13) so that the total stream of 6, 12 and 13 contains the desired molar amount of nitric acid (in mols of $HNO_3$) relative to the molar amount of the aromatic compounds (stream 1) and has the desired acid concentration (in % by weight of $HNO_3$).

The minimum molar amount of fresh nitric acid (stream 13) is determined by the amount of aromatic compounds employed (stream 1). However, as a result of side reactions and other losses, additional nitric acid is consumed, so that, in general, a molar excess of about 2 to about 25% of nitric acid is required.

The influence of the acid concentration of the fresh nitric acid to be employed on the acid concentration of the total stream (6, 12 and 13) is less the greater the amounts of acid from stream 6 and 12, that is to say the higher the chosen molar ratio of nitric acid to aromatic compound, which is to be set. Accordingly, acids of very diverse concentrations, for example dilute or concentrated nitric acid or azeotrope nitric acid, can also be employed as fresh acids.

Appropriately, the acid employed as fresh nitric acid (stream 13) is as concentrated as possible and has a concentration of > 90% by weight of $HNO_3$ and preferably of > 96% by weight, since the amount of water introduced with the acid has to be removed from the system in addition to the water of reaction and therefore gives rise to additional costs.

In addition, the desired acid concentration of the total stream consisting of stream 13, 12 and 6 can also be influenced by the ratio of streams 6 and 12, as well as by the acid concentration of the stream 13 of fresh nitric acid.

b. Nitration of the aromatic compounds
(Equipment A in FIG. 1)

The rate of reaction of the nitration increases as the temperature and the acid concentration rise and as the molar ratio increases. Identical rates of reaction can be obtained when high acid concentrations are combined with low temperatures and/or low molar ratios — or when high temperatures are combined with low acid concentrations and/or low molar ratios — or when high molar ratios are coupled with low temperatures and/or low acid concentrations.

Accordingly, high (low) rates of reaction are obtained with combinations of high (low) temperature, molar ratio and acid concentration values.

The lowest possible acid concentrations which still lead to satisfactory rates of reaction when the highest molar ratios are used depend on the reactivity of the aromatic compounds.

For naphthalene, according to the process of the invention a lower acid concentration limit of about 45% by weight results for molar ratios of nitric acid to the aromatic compound of about 5 : 1 and a lower acid concentration limit of 40% by weight results for molar ratios of about 50 : 1. Correspondingly, for mononuclear aromatic compounds a lower acid concentration limit of about 60% by weight results for molar ratios of nitric acid to the aromatic compound of about 5 : 1 and a lower acid concentration limit of about 45% by weight results for molar ratios of about 50 : 1.

The preferred ranges for the nitration of binuclear aromatic compounds are given by molar ratios of acid to aromatic compound of about 15 : 1 to about 6 : 1 and acid concentrations of 45 to 55% by weight of $HNO_3$. In the case of mononuclear aromatic compounds, the preferred molar ratios of acid to the aromatic compound are also about 15 : 1 to about 6 : 1 and the acid concentrations are 60 to 68% by weight of $HNO_3$.

During the nitration, nitrous acid and nitrous gases which partly remain dissolved in the acid, are formed to a slight extent. These compounds can be essential for starting the nitration reaction. Thus, for example, the nitration of naphthalene in about 40% strength by weight acid starts only when small amounts of nitrous acid or nitrous gases are present. When other aromatic compounds are nitrated or when higher acid concentrations are used this effect is less marked.

In general, however, the recycled acids (stream 6 and stream 12) contain a sufficient amount of dissolved nitrous gases or nitrous acid (>0.1% by weight), so that a separate addition of nitrite or nitrous gases will be advantageous only in special cases, for example when starting up.

The phase characteristics of the reaction mixture, that is to say whether the reaction mixture is wholly or partly in the form of a suspension, an emulsion or a solution, is physically determined by the — temperature dependent — solubility ratios of the aromatic compound and nitroaromatic compound in the 4-component system comprising $HNO_3/H_2O$/aromatic compound/nitro-aromatic compound.

At temperatures above the solidification point of the reaction mixture consisting of the aromatic compound, the nitro-aromatic compound and aqueous nitric acid, the nitrations can proceed entirely or partly in a homogeneous phase or entirely or partly with the formation of an emulsion. The ratio of homogeneous to heterogeneous phase characteristics can depend on the ratio of aromatic compound/nitro-aromatic compound and can shift in the course of the nitration to give greater proportions of emulsion.

By increasing the ratio of nitric acid to aromatic compound/nitro-aromatic compound on the one hand, such as by increasing the acid concentration of the nitric acid, and by raising the temperature on the other hand, it is possible to increase the solubility of aromatic compound/nitro-aromatic compound in the system, so that the proportion of suspension or emulsion declines in favour of the formation of a homogeneous liquid phase.

In principle, the nitrations in nitric acid can be carried out in suspension or emulsion or in homogeneous solution. In respect or thorough mixing and removal of the heat of reaction, nitrations in emulsion or a homogeneous phase are usually simpler to control. For working up, that is to say the separation of the organic product and the acid, it can, on the other hand, be advantageous if the reaction mixture is already obtained in two phases as an emulsion or suspension. In this case it is possible under certain circumstances partly or wholly to dispense with the dilution of the reaction mixture, which is otherwise necessary.

Continuous nitration can be carried out in the continuous reactors known industrially, for example in a single stage or multi-stage kettle cascade, in chamber, cell, tube and loop reactors or in combinations of these types of reactor, such as in a loop reactor with a downstream tube. (Apparatus A in FIG. 1).

In the case of a kettle cascade, the individual reactors can be run at different temperatures by a suitable arrangement of the coolant cycles. In principle, the same also applies in the case of tube, loop, cell or chamber reactors. Coolant cycles at different temperatures can be installed in this case also by subdividing the cooling jacket into various segments. Appropriately, the temperature control provided is such that the reaction is run at a higher reaction temperature towards the end of the conversion than at the start of the reaction in order to shorten the long reaction times taken to achieve a substantial or complete conversion. However, it must be taken into account that the extent to which secondary reactions, such as oxidation or dinitration, take place can also rise as the reaction temperature increases.

In order to direct the nitration of the educt in the main in the direction of mononitro products and in order to prevent any subsequent reaction to dinitro products in the case of the more reactive aromatic compunds, care must be taken that the residence time spectrum in the particular reactor is as narrow as possible. In the case of kettle cascades or a chamber or cell reactor, a higher number of stages and good stirring is therefore advantageous and in the case of the tube reactor plug flow, which can be achieved by suitable inserts and/or by good flow conditions (turbulent flow and Reynolds numbers of >> 2300), must be ensured.

However, if the danger of further nitration to dinitro compounds is slight, a narrow residence time spectrum or plug flow are not required to the same extent; however these remain desirable in order to save unnecessarily long reaction times. This is because the reaction time required for a given conversion becomes longer as the residence time spectrum becomes wider, or as the flow conditions shift in the direction of laminar flow.

The nitration is appropriately carried out only until the conversion of the starting material is such that only small amounts of secondary products (for example the dinitro product) are formed in addition to the desired mononitro product. This means that the reaction is discontinued at conversions of <100%, but preferably at conversions of >90%, and the unconverted starting material is separated off by a suitable method, for example by rectification of the organic crude product.

However, in those cases where the secondary product is not troublesome, the reaction is carried out to 100% conversion of the starting material and some formation of the secondary product is accepted.

c. Dilution
(Equipment B in FIG. 1)

In order to end the reaction at a specific degree of conversion under specific flow conditions, water and/or dilute nitric acid can be added to the reaction mixture in a mixing apparatus B. The water can be fed in from outside the process (stream 14) or can be taken from the top product of the column (stream 9).

However, since the amount of water additionally introduced by stream 14 leads to an increase in the amount of water in stream 10 (which may subsequently have to be fed to a biological purification unit or the like), it is more advisable to take the water from stream 9.

Likewise, it is also possible to add a dilute nitric acid in place of water and this acid can be taken from the rectifying section of the column via a sidestream take-off (stream 11). With this method the increased volumes during the dilution process and during phase separation, which necessitate larger apparatuses, may prove disadvantageous.

The dilution can be carried out in various apparatuses B, for example in single stage or multi-stage kettle cascades or in a mixing tube.

If solid phases are formed when the reaction mixture is diluted, single stage stirred kettle cascades or other mixing units suitable for the treatment of suspensions, for example loop reactors, are to be employed.

The operation will be carried out above the solidification point of the dilute reaction mixture when the melting point of the reaction products permits this, in order to achieve simpler mixing and transport and removal of the heat of dilution.

The degree of dilution of the reaction mixture which can be achieved by the addition of water and/or dilute nitric acid depends, firstly, on a phase separation into an organic phase and an inorganic phase being achieved at all and secondly on the content of organic products in the inorganic phase (stream 5) becoming small or disappearing completely.

The latter can be important when the dissolved amounts of nitro products which pass together with the inorganic phase (stream 7) into the sump of the $HNO_3$ column could be partially or completely further nitrated or oxidised by the nitric acid in the sump or could decompose on exposure to heat in the sump of the column. In the case of low concentrations of nitro products in the sump, reactions of this type would not be important since the heat of decomposition which would be evolved would easily be removed by the vaporisation process. Moreover, when the contents of dissolved nitro-aromatic compound are low there is a possibility that all of these can be distilled off, with the formation of an azeotrope with water, over the top of the column without great effort.

The dissolved amounts of nitro products which pass, together with the inorganic phase (stream 6), back into the nitration could also be further nitrated and thus lead to impairment in the selectivity of the reaction. However, when the contents of nitro product in stream 5 are low, these reactions also play only a minor role. The inorganic phase can be substantially to completely freed from the organic product by means of an appropriate lower of the acid concentration, by lowering the temperature or in some cases also by an extraction.

The aromatic compound to be nitrated can itself be employed as the extraction agent if its solubility in the nitric acid of stream 5 or 7 is low. In this case, the residual content of aromatic compound which remains would pass, together with the water, over the top of the column. In the case of higher contents, undesired reactions could occur in the sump of the column, as described above.

However, solvents which are inert towards sump nitric acid, for example chlorinated hydrocarbons, such as methylene chloride or dichloroethane, can also be employed as extraction agents. The extract containing the nitro products can be separated again by distillation.

d. Phase separation
(Equipment C in FIG. 1)

Phase separation of the nitration mixture is advantageously carried out at temperatures above the solidification point of the nitro compunds since the separation of liquid phases can generally be carried out with less expensive process technology than a separation of solid and liquid phases.

In general, the ease with which the liquid/liquid separation can be effected increases with decreasing temperature for the systems which can be used.

Static separators or centrifuges are examples of equipment which can be used for liquid/liquid phase separation and these can also very readily be operated continuously.

Depending on the product characteristics, known filter units, such as, for example, rotary pressure filters, chamber filters, filter presses and the like, can be used for solid/liquid phase separation.

e. Working up of the organic phase
(Equipment E and G in FIG. 1)

The organic phase can contain small amounts of dissolved nitric acid and undesired by-products (mainly those containing phenolic hydroxyl groups). Whilst the nitric acid is advantageously washed out by water (stream 19) (equipment E 1), the by-products containing phenolic hydroxyl groups can be removed by washing (equipment E 2) with dilute sodium hydroxide solution or sodium carbonate solution (stream 29). In the case of nitro-aromatic compounds which are present as liquids at temperatures of up to about 100° C, so-called mixer/settlers, in which intensive stirring of the phases and phase separation can be carried out in combination as a multi-stage operation in one apparatus, are suitable as the equipment E.

After washing, the organic phase can be freed from unconverted starting material and where appropriate from residual water by rectification in a column G. It is also possible to carry out direct distillation of the organic nitric acid-containing phase without prior washing and in this case the nitric acid is removed over the top together with the still unconverted aromatic hydrocarbons.

If the nitro-aromatic compounds are in a solid form, the phases are generally stirred by means of stirring units. The phases are separated with the aid of suitable filter equipment or sedimentation equipment.

f. Flow route of the inorganic phase

A partial stream 7 from the inorganic phase (stream 5) obtained after phase separation is fed through the column which is at least of such a size that it is possible to take off over the top of the column the amount of water which corresponds to the sum of the water of reaction, the water contained in the fresh nitric acid (stream 13) and the water which may be contained in the nitric acid added for dilution (stream 11), or to the water added via stream 14 or 9 less the water removed from the system with stream 4. The remainder of the inorganic phase (stream 6) is recycled direct to the nitration.

In principle, of course, it is also possible to feed the entire stream 5 through the column; in this case (stream 6 = zero), however, a larger and thus more expensive column would be required.

g. Rectification of the inorganic phase (Equipment D in FIG. 1)

The rectification of the inorganic phase (stream 7) for removal of the water of reaction from the system can be carried out in a column which is fitted, for example, with sieve trays or bubble cap trays, fabric packing or tower packing. The rectification can be carried out under normal pressure or under a vacuum of about 500 to 10 mm Hg in order to keep the sump temperature low. The reflux ratio depends on the number of stripping trays and rectifying trays and on the concentration of the feed and take-offs and is approximately in the range from 1 to 10. The distribution of water and nitric acid over the profile of the column depends on the operating conditions of the column, for example on the concentrations of the feed and take-offs, on the operating pressure, on the temperature profile in the stripping section and the rectifying section and on the reflux ratio. By appropriate choice of these operating conditions it is possible to take off nitric acid-free water at the top of column, a nitric acid which is more dilute than the feed from the rectifying section and a nitric acid which is more concentrated than the feed and at most a nitric acid containing up to about 68% by weight of $HNO_3$ from the stripping section or the sump. The maximum acid concentration of the sump discharge is determined by the composition of the azeotrope nitric acid, which is pressure-dependent to a slight extent. Thus, the azeotrope contains about 68% by weight of $HNO_3$ 760 mm Hg, about 66.5% by weight of $HNO_3$ at 200 mm Hg and about 64.5% by weight of $HNO_3$ at 50 mm Hg.

Process Variants

A particular embodiment (varient 1, compare FIG. 2) of the process according to the invention consists in carrying out both the dilution and the phase separation in two stages, the first dilution (B 1) and phase separation ($C_1$) being carried out at an acid concentration such that phase separation into an inorganic phase and an organic phase just takes place. After the phase separation, part of the inorganic phase is recycled direct to the nitration and part is further diluted (B 2) and by this means the amounts of organic product previously still contained in solution in a small amount are precipitated and then separated off (C 2).

Figure 2:
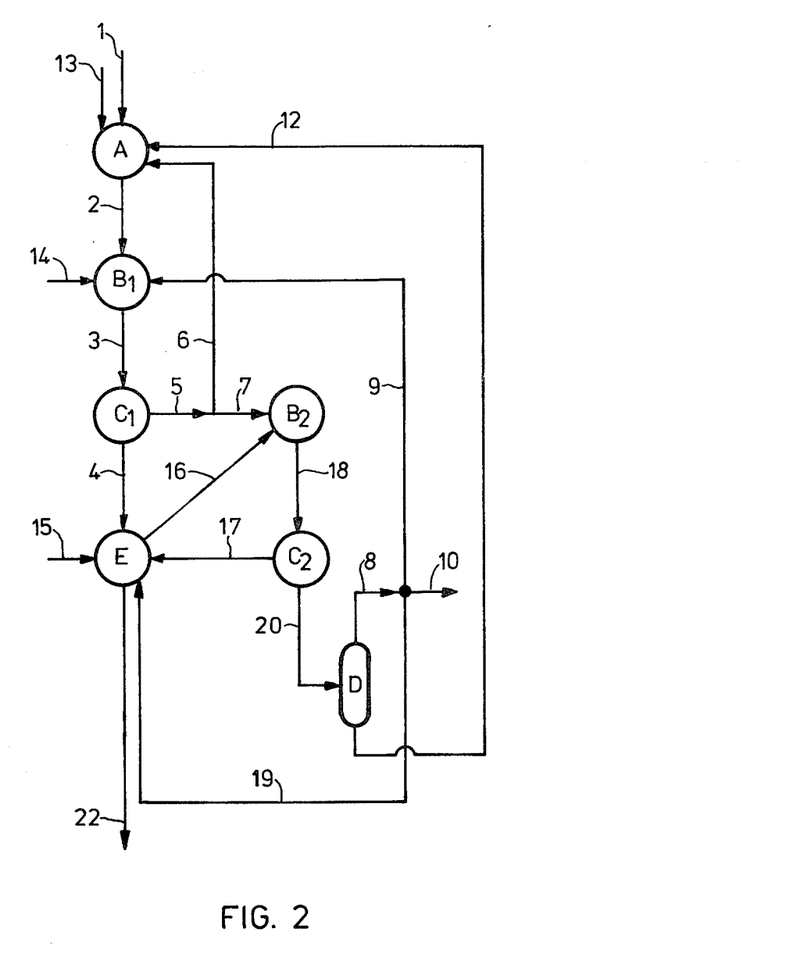

The residual inorganic phase is fed to the rectification stage (D); the stream of water which goes off over the top in this stage is optionally used for the dilution stage (B 1) or for washing (E) the organic end product. An amount which corresponds to the water of reaction is withdrawn from the system and the sump nitric acid (stream 12) taken from the sump during the rectification (D) is recycled to the nitration.

With this variant, streams 1 to 14 have the meaning already discussed in relation to FIG. 1. In this case-differing from FIG. 1 — the partial stream 7 of stream 5 (inorganic phase) obtained after the phase separation is fed to column (D) only after dilution with the wash water from the wash (E) of the organic phase (stream 16) and subsequent phase separation (C2) into an inorganic phase (stream 20) and an organic phase (stream 17), which is recycled into the washing unit for the organic phase. The water (stream 8) taken off over the top of the column (D) is used for dilution (B 1) (stream 9) and for washing (E) the organic phase (stream 19) and some of this water — corresponding to the amount of water of reaction formed — must be removed from the system. Water can additionally be fed into the process via steam 14 or 15 but this increases the stream of effluent 10.

This operation of the process represents a variant of the process shown in FIG. 1 inasmuch as, in this case, the first dilution ($B_1$) (stream 2, stream 3) is carried out only until the acid concentration is just such that separation into an organic phase and an inorganic phase takes place. However, in this case the inorganic phase as a rule still contains small amounts of organic product in solution and in this variant these are separated off after further dilution (B 2) of the acid, by which means the solubility of the organic products is reduced, and subsequent phase separation.

The small amount of organic product still contained in solution in the partial stream 6, which is directly recycled, of the inorganic phase does not lead to any discernible deterioration in the product quality in the nitration stage if the content of organic product in stream 6 is, for example in the case of nitrotoluene, less than 5% by weight. Otherwise, it is possible to adjust the content to this value by appropriate dilution of stream 2 with the aid of stream 9 or 14.

Figure 3:
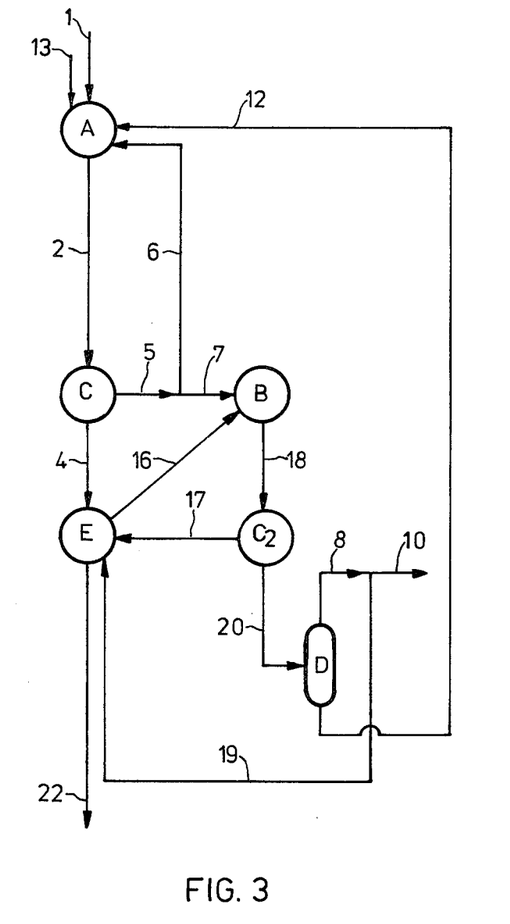

Another embodiment (variant 2) of the process according to the invention furthermore consists in carrying out the nitration of the aromatic compound using an acid concentration and a molar ratio of acid to aromatic compound such that, after the desired conversion of the starting material, the reaction mixture separates into two phases as a result of the dilution by the water of reaction and, if necessary, by lowering of the temperature, separating part or all of the organic phase, in accordance with variant 1, through a column (D) into water and a fraction with a higher nitric acid content and withdrawing an amount which corresponds to the water of reaction from the system. This variant is shown in FIG. 3.

Both variants are advantageous for the preparation of, for example, nitronaphthalene, nitrotoluene and nitrobenzene.

The nitration can be carried out — very simply in these cases — in such a way that phase separation takes place towards the end of the reaction as a result of the dilution by the water of reaction and this separation is further intensified by lowering the temperature, say to about room temperature.

The organic phase contains nitric acid and water in solution — in an amount corresponding to the temperature-dependent and acid concentration-dependent solubility equilibrium between aqueous nitric acid and the nitro-aromatic compound. This nitric acid content in the organic phase is now not lost according to the process of the invention but passes, together with the wash water (stream 16) necessary for washing the organic end product, via the dilution stage (B) and the phase separation (C 2) into the rectification stage (D) and from there passes back, in the form of, for example, azeotrope nitric acid, into the nitration.

Figure 4:
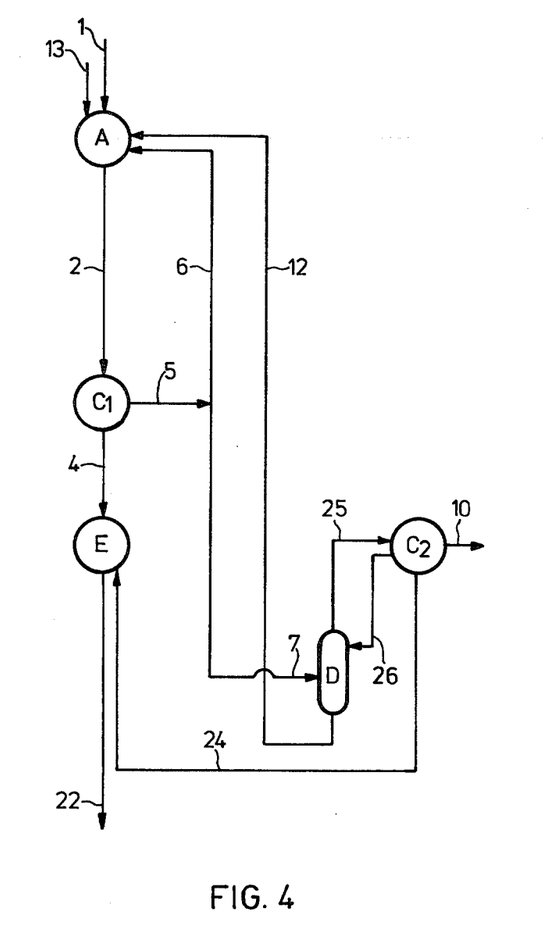

A further embodiment (varient 3) of the process according to the invention is shown in FIG. 4, in which streams 1 to 22 have the meaning indicated in relation to FIG. 3.

This variant is characterised in that, under the conditions of the separation by distillation of water in column (D), the nitro-aromatic compound (in some cases together with still unconverted starting material) dissolved in small amounts in stream 7 also passes (stream 25) over the top and, after it has been separated off, for example by phase separation (C 2), is then combined with the bulk of the nitro-aromatic compound via stream 24. The reflux (stream 26) consists of water.

This variant is possible in, for example, the case of nitrobenzene, nitroxylene, nitrotoluene, nitrochlorobenzene and nitronaphthalene since, under the rectification conditions, these compounds can, by forming an azeotrope with water, pass over the top. With this variant, the nitration and separation are appropriately so carried out that the content of organic product in stream 5 or stream 7 is as low as possible. This can be effected as in the variants described above.

Figure 5:
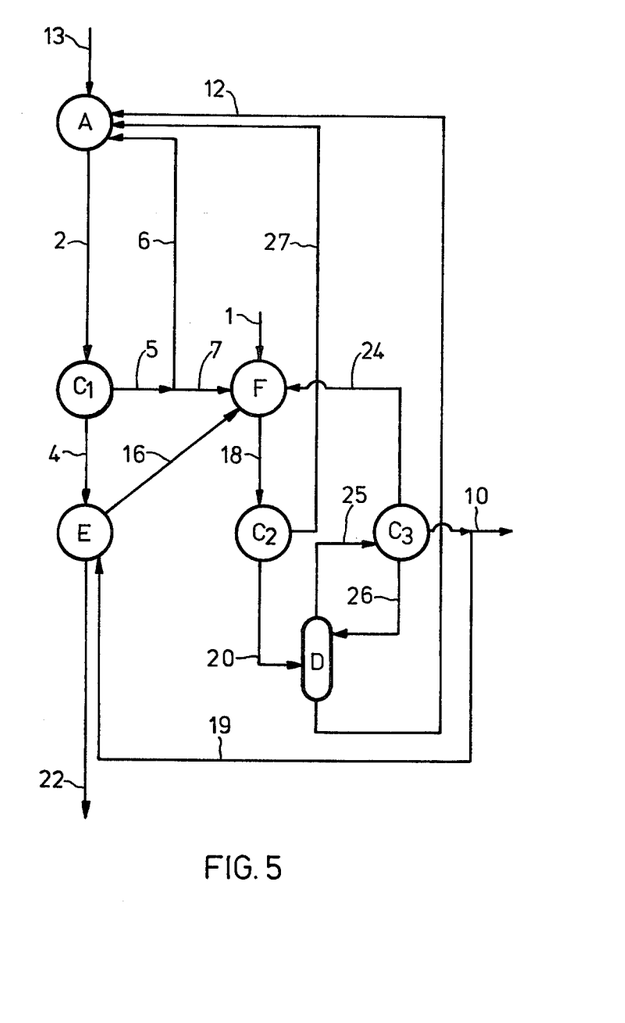

A further embodiment (variant 4) of the process according to the invention is shown in FIG. 5, in which streams 1 to 26 have the meaning indicated in block diagrams 3 and 4.

This variant is characterised in that the mixture obtained after combining partial stream 7 (inorganic phase) and the wash water from the organic phase (stream 16) is stirred thoroughly (F) with the aromatic compounds to be nitrated (stream 1) in order to extract the amounts of organic compounds dissolved in stream 7 and the mixture is then separated by phase separation (C 2), the inorganic phase (stream 20) being fed to column (D) and the organic aromatic phase (stream 27) which is charged with the nitro-aromatic compound, being fed to the nitration (A). In this case, the small residual amounts of aromatic compound and nitro-aromatic compound dissolved in stream 20 pass, as described in variant 3, over the top and, after phase separation (C 3) (stream 24), are re-used for the stirring operation (F). Water is passed, as reflux (stream 26), to the column, as described in varient 3.

Figure 6:
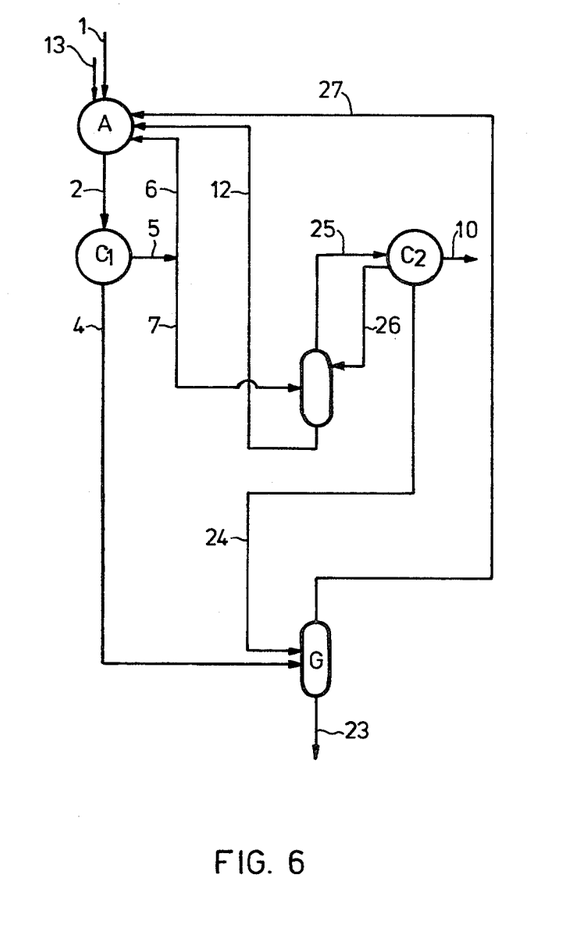

A further embodiment (variant 5) of the process according to the invention is shown in FIG. 6, in which streams 1 to 26 have the meaning indicated in relation to FIGS. 1 to 4.

This variant of the process according to the invention consists in following the procedure of variant 3 for the nitration of the aromatic compound and for the phase separation into an organic phase (stream 4) and an inorganic phase (stream 5), but the nitric acid contained in solution in the organic phase (stream 4) is also distilled over the top in a downstream nitro-aromatic column (G) for separating off, by distillation, organic starting material which has not been nitrated, and the resulting top product (stream 27) is re-employed in the nitration. The nitro-aromatic compound is obtained as the sump product (stream 23). Under the conditions of the distillation, partial reaction of the nitric acid with the aromatic compound which has not been nitrated can take place, especially at higher distillation temperatures. The organic product (stream 24) which passes over the top during rectification (D) of the inorganic phase and is obtained after phase separation (C 2) is fed direct into the rectification (G) of the organic phase.

Compared with the other known embodiments of the process according to the invention, this variant 5 has the advantage that the amounts of water to be distilled are smaller and the costs incurred are thus lower.

Figure 7:
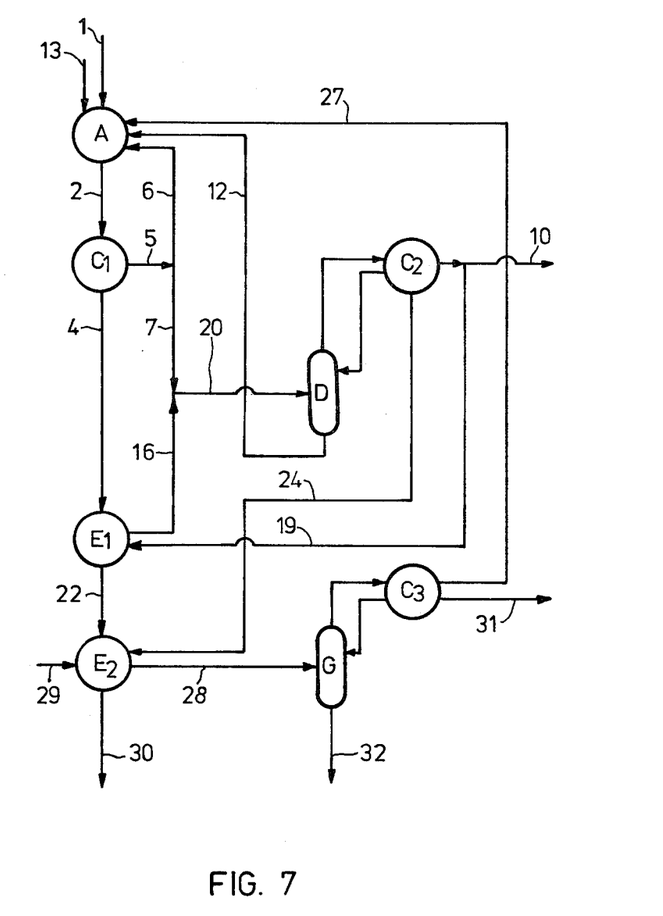

A further embodiment (variant 6) of the process according to the invention is shown in FIG. 7, in which streams 1 to 27 have the meaning indicated in relation to FIGS. 1 to 6. With this variant, the nitric acid dissolved in the organic phase (stream 4) is largely washed out (E 1) with a little water (stream 19). The resulting stream 16 is fed, together with partial stream 7 of the inorganic phase, into column (D). The residual content of nitric acid in the organic phase (stream 22) is washed out (stream 30) with dilute sodium carbonate solution or dilute sodium hydroxide solution (stream 29) in a second washing unit (E 2). Any by-products containing hydroxyl groups which may have been formed are also dissolved out during this operation.

The water-containing, moist organic phase (stream 28) is then freed from unconverted aromatic compounds and water in the nitro-aromatic compound (G). The unconverted aromatic compound (stream 27) is recycled to the nitration and the aqueous phase (stream 31) is withdrawn from the system.

Compared with variant 5, this variant has the advantage that any by-products containing hydroxyl groups which may be present and can interfere during the distillation are separated off prior to the rectification (G) of the organic phase.

With all the variants described, stream 6 can, in principle, also be zero; that is to say the entire inorganic phase can be fed into column (D), which is provided for rectification of the inorganic phase. In this case, the sump discharge concentration of stream 12 is a function of the desired water take-off over the top and of the amount and concentration of the feed. The number of separation stages required in the stripping section of the column is then smaller, since the concentration which results in the sump discharge is usually lower than in the case of the variants described. On the other hand, however, the dimensions of the column must be greater because of the higher throughputs.

It is, of course, possible to combine all of the variants mentioned with one another.

An essential advantage of the process according to the invention over the known mixed acid process is that no sulphuric acid, which gives rise to economic and ecological disadvantages, is used.

Moreover, compared with the known nitrations with excess nitric acid, the process according to the invention is safer, since the organic phase is separated off mechanically prior to rectification of the inorganic phase and the reaction is carried out with more dilute nitric acid ($\leq 68\%$ by weight) in place of concentrated nitric acid ($\sim 96$–$98\%$). Furthermore, compared with the known processes, the process according to the invention has the advantage that the nitric acid is cycled in a virtually loss-free manner without it being necessary to withdraw nitric acid from the system in order to maintain the cycle volume. A further advantage of the process is that the amount of unconverted aromatic compound cycled can be kept very small or zero and this leads to a lowering of the evaporation costs.

In addition, the process according to the invention displays good space-time yields which are higher than those for reactions which proceed at the boundary phase between a gaseous and a liquid phase. The reaction times (<30 minutes), which are considerably shorter than those in the known process, make it possible for the first time economically to employ reactors which operate continuously.

EXAMPLE 1

(Route of the material streams: compare FIG. 4)

516 g/hour of a 66% strength by weight nitric acid and 68.5 g/hour of toluene (molar ratio of nitric acid to the aromatic compound 7.3 : 1) are reacted continously at 70° C and with a residence time of 10 minutes in a tube reactor which can be cooled well. The reaction mixture is then cooled and continuously separated, at 30° C, into an inorganic phase and an organic phase in a separator (C 1).

Part (about 334 g/hour) of the inorganic phase is recycled direct into the nitration reactor (A) and the other part (about 144 g/hour) is fed continuously to a column (D), which is operated under normal pressure and at a temperature at the top of 95° to 100° C.

The stream which is taken off over the top of the column is divided, after phase separation, into three parts, one part (stream 26: water) being fed as reflux to the column, one part (stream 10: about 11 ml/hour of water) being withdrawn from the system and the other part (stream 24: about 2 g/hour of nitrotoluene) being combined with the organic phase.

The sump discharge from the column (about 131 g/hour of 66% strength by weight nitric acid) is fed, together with 55.7 g/hour of a 98% strength by weight fresh nitric acid, to the nitration reactor. Together with the directly recycled part of the inorganic phase, these two streams provide the nitric acid feed, described initially, for the nitration.

After washing with water, the organic phase is twice washed with one and a half times the amount of 2% strength by weight sodium hydroxide solution and then washed with water until neutral and, by rectification in a column, freed from unconverted starting material and water, which are taken off over the top.

Yield: 100 g/hour of nitrotoluene of the following composition (in % by weight):
4-nitrotoluene; 38.8
3-nitrotoluene; 5.5
2-nitrotoluene; 55.7
corresponding to 98% of theory of nitrotoluene.

EXAMPLE 2

(Route of the material streams: compare FIG. 6)

515 g/hour of a 66% strength by weight nitric acid and 68.5 g/hour of toluene (molar ratio of nitric acid to the aromatic compound 7.3 : 1) are reacted continuously at 70° C and with a residence time of 25 minutes in a cascade consisting of two loop reactors. The reaction mixture is then cooled and continuously separated (C 1), at 30° C, into an inorganic phase and an organic phase in a separator (C 1).

Part (about 292 g/hour) of the inorganic phase is recycled direct into the nitration reactor (A) and the other part (about 186 g/hour) is fed continuously to a column (D), which is operated under 760 mm Hg and at a temperature at the top of 100° C.

The stream which is taken off over the top of the column and is free from nitric acid is withdrawn from the system after the nitrotoluene which has distilled over together with the water has been separated off (about 3 g/hour of nitrotoluene) by phase separation (C 2) (about 14 ml/hour of water withdrawn from the system).

The sump discharge from the column (about 169 g/hour of 66% strength by weight nitric acid) is fed, together with 50.3 g/hour of a 98% strength by weight fresh nitric acid, to the nitration reactor.

The organic, nitric acid-containing phase (about 106 g/hour) is fed to a column which is operated under about 25 mm Hg (sump temperature about 170° C) in which unconverted toluene and nitric acid (about 8 g/hour) are withdrawn over the top (stream 27) and recycled to the nitration and in which 100 g/hour of nitrotoluene are withdrawn from the sump.
Composition in % by weight
4-nitrotoluene; 38.7
3-nitrotoluene; 5.6
2-nitrotoluene; 55.7
corresponding to 98% of theory of nitrotoluene.

EXAMPLE 3

(Route of the material streams: FIG. 3)

1,605 g/hour of a 46.5% strength by weight nitric acid, which contains about 0.1% by weight of nitrous acid, and 288 g/hour of molten naphthalene (molar ratio of nitric acid to the aromatic compound 5.3 : 1) are reacted continuously at 60° C and with a residence time of 60 minutes in a two-stage stirred kettle cascade. The reaction mixture is then continuously separated, at 60° C, into an inorganic phase and an organic phase in a static separator (C1). The organic phase is washed (E) with water (about 182 ml/hour).

Part (about 1,199 g/hour) of the inorganic phase is recycled direct to the nitration reactor (A) and the other part (about 236 g/hour) is diluted with the wash water (about 246 ml/hour) which has been obtained from the wash (E) of the organic phase. Residues of organic product which were dissolved in the inorganic phase then precipitate out and are separated off (C2) and combined with the bulk of the nitro-aromatic compound.

The inorganic phase (stream 20) which remains after this separation is fed continuously to a column (D) which is operated under 400 mm Hg and at a temperature at the top of 80° C.

The nitric acid-free stream of water taken off over the top of the column is used for washing the organic phase, as described above, and part (about 40.5 ml/hour) is withdrawn from the system.

The sump discharge from the column (about 259 g/hour of 46.5% strength by weight nitric acid) is fed, together with 150 g/hour of a 98% strength by weight fresh nitric acid, to the nitration reactor (A). Together with the directly recycled part of the inorganic phase, these two streams provide the nitric acid feed, described initially, for the nitration.

After washing with water (E) the organic phase (stream 22) is twice washed with one and a half times the amount of 2% strength by weight sodium carbonate solution and then washed with water until neutral and dried in a falling film drier. Yield: 385 g/hour of nitronaphthalene (95.6% by weight of 1-nitro-naphthalene, 4.3% by weight of 2-nitro-naphthalene and 0.1% by weight of dinitronaphthalene), corresponding to a theoretical yield of 98.8% of nitronaphthalene.

EXAMPLE 4

(Route of the material streams: compare FIG. 3)

1,606 g/hour of a 46.5% strength by weight nitric acid, which contains 0.2% by weight of nitrous acid, and 288 g/hour of molten naphthalene (molar ratio of nitric acid to the aromatic compound 5.3 : 1) are reacted continuously at 70° C and with a residence time of 30 minutes in a two-stage stirred kettle cascade. The reaction mixture is then continuously separated, at 65° C, into an inorganic phase and an organic phase in a static separator. The organic phase is washed with water (about 35 ml/hour).

Part (about 1,399 g/hour) of the inorganic phase is recycled direct to the nitration reactor and the other part (about 37 g/hour) is diluted with the wash water (about 98 ml/hour) which has been obtained from the wash (E) of the organic phase. Residues of organic product dissolved in the inorganic phase then precipitate out and these are separated off (C2) and combined with the bulk of the nitro-aromatic compound.

The inorganic phase (stream 20) which remains after the separation is fed continuously to a column (D) which is operated under 760 mm Hg and at a temperature at the top of 100° C.

Part of the nitric acid-free stream of water taken off over the top of the column is used for washing (E) the organic phase, as described above, and the other part of this stream (41 ml/hour) is withdrawn from the system.

The sump discharge from the column (about 61 g/hour of 67% strength by weight nitric acid) is fed, together with 152 g/hour of a 98% strength by weight fresh nitric acid, to the nitration reactor. Together with the directly recycled part of the inorganic phase, these two streams provide the nitric acid feed, described initially, for the nitration.

After washing with water (E), the organic phase (stream 22) is twice washed with one and a half times the amount of 2% strength by weight sodium carbonate solution and is then washed with water until neutral and dried in a falling film drier. Yield: 381.5 g/hour of nitronaphthalene (95.4% by weight of 1-nitronaphthalene, 4.4% by weight of 2-nitronaphthalene and 0.2% by weight of dinitronaphthalene), corresponding to a theoretical yield of 97.8% of mononitronaphthalene.

EXAMPLE 5

(Route of the material streams: compare FIG. 2)

2,530 g/hour of a 50% strength by weight nitric acid, which contains 0.4% by weight of nitrous acid, and 256 g/hour of molten naphthalene (molar ratio of nitric acid to the aromatic compound 10.1/1) are reacted continuously at 70° C and with a residence time of about 1.5 minutes in a tube reactor. The reaction mixture is then diluted (B1) with 405 ml/hour of water, the dilution also being continuous, and continuously separated, at 60° C, into an inorganic phase and an organic phase in a separator (C1). The organic phase is washed (E) with water (stream 19, about 832 ml/hour).

Part (about 339 g/hour) of the inorganic phase (stream 5) is recycled direct to the nitration reactor and the other part (about 2,497 g/hour) is diluted (B2) with the wash water (stream 16, about 838 ml/hour) which has been obtained from the wash of the organic phase. Residues of organic product dissolved in the inorganic phase then precipitate out and are separated off (C2) and combined with the bulk of the nitroaromatic compound (stream 17).

The inorganic phase (stream 20) which remains after the separation is fed continuously to a column (D) which is operated under 100 mm Hg and at a temperature at the top of 44° C.

The nitric acid-free stream of water taken off over the top of the column is divided into three parts, one part being used to dilute the reaction mixture (B1), one part being used to wash the organic phase (E), as described above, and the other part (about 94.3 ml/hour) being withdrawn from the system.

The sump discharge from column (D) (that is to say about 1,997 g/hour of 50% strength by weight nitric acid) is fed, together with 194 g/hour of a 69% strength by weight fresh nitric acid, to the nitration reactor. Together with the directly recycled part of the inorganic phase, these two streams provide the nitric acid feed, described initially, for the nitration.

After washing with water (E), the organic phase (stream 22) is twice washed with one and a half times the amount of 2% strength by weight sodium carbonate solution and is then washed with water until neutral and dried in a falling film drier operated at 100° C and under 200 mm Hg. Yield: 339 g/hour of nitronaphthalene (95.4% of 1-nitronaphthalene, 4.4% of 2-nitronaphthalene and 0.2% of dinitronaphthalene), corresponding to a theoretical yield of 97.9% of nitronaphthalene.

EXAMPLE 6

(Route of the material streams: compare block diagram No. 3)

1,849 g/hour of a 68% strength by weight nitric acid and 184 g/hour of toluene (molar ratio of nitric acid to the aromatic compound 10 : 1) are reacted continuously at 70° C and with a residence time of 3 minutes in a tube reactor. The reaction mixture is then cooled and continuously separated, at 20° C, into an inorganic phase and an organic phase in a separator. The organic phase is washed with water (about 756 ml/hour).

Part (about 1,116 g/hour) of the inorganic phase is recycled direct to the nitration reactor and the other part (about 585 g/hour) is diluted with the wash water (about 848 ml/hour) which has been obtained from the wash of the organic phase. Residues of organic product dissolved in the inorganic phase then precipitate out and these are separated off and combined with the bulk of the nitro-aromatic compound.

The inorganic phase which remains after this separation is fed continuously to a column (D) which is operated under 760 mm Hg and at a temperature at the top of 100° C.

The nitric acid-free stream of water taken off over the top of the column is divided into two parts after the nitrotoluene, which has distilled over in traces, has been separated off and one part is used for washing the organic phase, as described above, and the other part (about 36 ml/hour) is withdrawn from the system.

The sump discharge from the column (about 626 g/hour of 68% strength by weight nitric acid) is fed, together with 135 g/hour of a 98% strength by weight fresh nitric acid, to the nitration reactor. Together with the directly recycled part of the inorganic phase, these two streams provide the nitric acid feed, described initially, for the nitration.

After washing with water, the organic phase is twice washed with one and a half times the amount of 2% strength by weight sodium hydroxide solution and is then washed with water until neutral and freed, by rectification in a column, from uncoverted starting material and water, which are taken off over the top.

Yield: 267 g/hour of nitrotoluene of the following composition (in % by weight):
4-nitrotoluene; 38.8
3-nitrotoluene; 5.4
2-nitrotoluene; 55.8
corresponding to a theoretical yield of 97.4% of nitrotoluene.

EXAMPLE 7

(Route of the material steams: compare block diagram No. 2)

1,389 g/hour of a 65% strength by weight nitric acid and 184 g/hour of toluene (molar ratio of nitric acid to the aromatic compound 7.2 : 1) are reacted continuously at 58° C and with a residence time of 50 minutes in a three-stage stirred kettle cascade. The reaction mixture is then diluted with 423 ml/hour of water, the dilution also being continuous, and cooled and continuously separated, at 30° C, into an inorganic phase and an organic phase in a separator. The organic phase is washed with water (about 700 ml/hour).

Part (about 316 g/hour) of the inorganic phase is recycled direct to the nitration reactor and the other part (about 1,278 g/hour) is diluted with the wash water (about 829 ml/hour) which has been obtained from the wash of the organic phase. Residues of organic product dissolved in the inorganic phase then precipitate out and these are separated off and combined with the bulk of the nitro-aromatic compound.

The inorganic phase which remains after this separation is fed continuously to a column which is operated under 760 mm Hg and at a temperture at the top of 100° C.

The nitric acid-free stream of water taken off over the top of the column is divided into three parts after the nitrotoluene which has distilled over in traces has been separated off and one part is used to dilute the reaction mixture, one part is used to wash the organic phase, as described above, and the other part (36 ml/hour) is withdrawn from the system.

The sump discharge from the column (about 940 g/hour of 67% strength by weight nitric acid), which has been freed from organic product, is fed, together with 135 g/hour of a 98% strength by weight fresh nitric acid, to the nitration reactor. Together with the directly recycled part of the inorganic phase, these two streams provide the nitric acid feed, described initially, for the nitration.

After washing with water, the organic phase is twice washed with one and a half times the amount of 2% strength by weight sodium carbonate solution and is then washed with water until neutral and freed, by rectification in a tray column, from unconverted starting material and water, which are taken off over the top.

Yield: 271 g/hour of nitro-toluene of the following composition (in % by weight):
4-nitrotoluene, 38.9
3-nitrotoluene, 5.5
2-nitrotoluene 55.6
corresponding to a theoretical yield of 98.9% of nitrotoluene.

EXAMPLE 8

(Route of the material streams: compare FIG. 5)

708 g/hour of a 66% strength by weight nitric acid and 68.5 g/hour of toluene which has been used for stirring with stream 7 (molar ratio of nitric acid to the aromatic compound 10 : 1) are reacted continuously at 60° C and with a residence time of 20 minutes in a cascade consisting of two loop reactors. The reaction mixture (stream 2) is then cooled and continuously separated, at 30° C, into an inorganic phase (stream 5) and an organic phase (stream 4) in a separator. The organic phase is washed with water (stream 19; about 34 ml/hour).

Part (stream 6: about 424 g/hour) of the inorganic phase is recycled direct to the nitration reactor and the other part (stream 5: about 225 g/hour) is fed, together with the wash water (about 68 ml/hour) from the wash of the orgnaic product (stream 16), to a loop reactor (F) which has intense circulation, for stirring with 68.5 g/hour of toluene (stream 1). The mixture is then divided in a separator (C2) into an organic phase (stream 27), which is fed to the nitration reactor, and an inorganic phase (stream 20), which is fed to a column (D) with fabric packing and is operated under 760 mm Hg and a temperature at the top of 100° C. The top product from this column is separated by phase separation (C3) into an organic phase (stream 24) which is recycled for the stirring operation, and an aqueous phase, part of which is used for washing the organic phase (stream 19) and part of which (stream 10, about 14.3 ml of water/hour) is withdrawn from the system.

The sump discharged from column (D) (about 241 g/hour of 66% strength by weight nitric acid) is fed, together with 50.3 g/hour of a 98% strength by weight fresh nitric acid, to the nitration reactor. Together with the directly recycled part of the inorganic phase (stream 6), these two streams provide the nitric acid feed, described initially, for the nitration.

After washing with water, the organic phase is twice washed with one and a half times the amount of 2% strength by weight sodium hydroxide solution and is then washed with water until neutral and dried in a falling film drier.

Yield: 100 g/hour of nitrotoluene Composition in % by weight:
4-nitrotoluene 38.8
3-nitrotoluene 5.6
2-nitrotoluene 55.6
corresponding to a theoretical yield of 98% of nitrotoluene.

EXAMPLE 9

(Route of the material streams: compare FIG. 3)

3,193 g/hour of a 67% strength by weight nitric acid and 212 g/hour of 1,3-xylene (molar ratio of nitric acid to the aromatic compound 17 : 1) are reacted continuously at 50° C and with a residence time of 12 minutes in a three-stage stirred kettle cascade. The reaction mixture is then cooled and continuously separated, at 25° C, into an inorganic phase and an organic phase in a separator. The organic phase is washed with water (about 919 ml/hour).

Part (about 2,312 g/hour) of the inorganic phase is recycled direct to the nitration reactor and the other part (about 693 g/hour) is diluted with the wash water (about 1,020 g/hour) which has been obtained from the wash of the organic phase. Residues of organic product dissolved in the inorganic phase then precipitate out and these are separated off and combined with the bulk of the nitro-aromatic compound.

The inorganic phase which remains after this separation is fed continuously to a column (D) which is operated under 760 mm Hg and at a temperature at the top of 100° C.

The nitric acid-free stream of water taken off over the top of the column is divided into two parts after the nitroxylene which has distilled over in traces has been separated off and one part is used to wash the organic phase, as described above, and the other part (36 ml/hour) is withdrawn from the system.

The sump discharge from column (D) (about 754 g/hour of 68% strength by weight nitric acid) is fed, together with 139 g/hour of a 98% strength by weight fresh nitric acid, to the nitration reactor. Together with the directly recycled part of the inorganic phase, these two streams provide the nitric acid feed, described initially, for the nitration.

After washing with water, the organic phase is twice washed with one and a half times the amount of 2% strength by weight sodium hydroxide solution and is then washed with water until neutral and freed, by rectification in a column, from unconverted starting material and water, which are taken off over the top.

Yield: 287 g/hour of nitro-xylene which consists to the extent of 16.5% by weight of 2-nitro-1,3-xylene and to the extend of 83% by weight of 4-nitro-1,3-xylene.

Theoretical yield of nitroxylene: 94.6%

If 1,4-xylene is employed in place of 1,3-xylene, this gives, under the conditions described, 287 g of 2-nitro-1,4-xylene in approximately 92% by weight purity.

EXAMPLE 10

(Route of the material streams: combination of FIGS. 1, 2 and 4)

1,881 g/hour of a 67% strength by weight nitric acid and 156 g/hour of benzene (molar ratio of nitric acid to the aromatic compound 10 : 1) are reacted continuously at 70° C and with a residence time of 45 minutes in a three-stage kettle cascade. The reaction mixture is then diluted with 98 ml/hour of water, this dilution also being continuous, and continuously separated, at 40° C, into an inorganic phase and an organic phase in a separator. The organic phase is washed with water (about 164 ml/hour).

The entire inorganic phase is diluted with the wash water (about 246 g/hour) which has been obtained from the wash of the organic phase and is fed continuously to a column which is operated under 760 mm Hg and at a temperature at the top of 100° C.

The nitric acid-free stream of water taken off over the top of the column is divided into three parts after separating off the nitrobenzene which has distilled over (about 70 g/hour) and one part is used to dilute the reaction mixture, one part is used to wash the organic phase, as described above, and the other part (about 98 ml/hour) is withdrawn from the system.

The sump discharge from the column (about 168.5 g/hour of 67% strength by weight nitric acid) which is free from organic product is fed, together with 195 g/hour of a 68% strength by weight fresh nitric acid, to the nitration reactor. Together with the directly recycled part of the inorganic phase, these two streams provide the nitric acid feed, described initially, for the nitration.

After washing with water, the organic phase is twice washed with one and a half times the amount of 2% strength by weight sodium hydroxide solution and is then washed with water until neutral and freed, by rectification in a column, from unconverted starting material and water, which are taken off over the top.

Yield: 241 g/hour of nitrobenzene (99.9% pure), corresponding to a theoretical yield of 97.9%.

EXAMPLE 11

(Route of the material streams: combination according to FIGS. 1, 2 and 4)

1,196 g/hour of a 67% strength by weight nitric acid and 71.4 g/hour of chlorobenzene (molar ratio of nitric acid to the aromatic compound 20 : 1) are reacted continuously at 90° C and with a residence time of 30 minutes in a tube reactor in which there is turbulent flow. The reaction mixture is then diluted with 281 ml/hour of water, this dilution also being continuous, and separated, at 30° C, by continuous filtration into an inorganic phase and an organic phase. The organic phase is washed with water (about 60 ml/hour).

Part (about 123 g/hour) of the inorganic phase is recycled direct to the nitration reactor and the other part (about 1,287 g/hour) is diluted with the wash water (about 90 ml/hour) which has been obtained from the wash of the organic phase and is fed continuously to a column which is operated under 760 mm Hg and at a temperature at the top of 100° C.

The nitric acid-free stream of water taken off over the top of the column is divided into three parts after separating off nitrochlorobenzene which has also distilled over (about 9 g/hour) and one part is used to dilute the reaction mixture, one part is used to wash the organic phase, as described above, and the other part (about 15 to 16 ml/hour) is withdrawn from the system.

The sump discharge from the column (about 1,011 g/hour of 67% strength by weight nitric acid) is fed, together with 62.5 g/hour of a 98% strength by weight fresh nitric acid, to the nitration reactor. Together with the directly recycled part of the inorganic phase, these two streams provide a nitric acid feed, described initially, for the nitration.

After washing with water, the organic phase is twice washed with one and a half times the amount of 2% strength by weight sodium carbonate solution and is then washed with water until neutral and freed, by rectification in a column, from unconverted starting material and water, which are taken off over the top.

Yield: 99.5 g/hour of nitrochlorobenzene of the following composition (% by weight):
o-nitrochlorobenzene; 37.0
m-nitrochlorobenzene; 0.8
p-nitrochlorobenzene; 62.2
corresponding to a theoretical yield of 99.5% of nitrochlorobenzene.

EXAMPLE 12

(Route of the material streams: compare FIG. 5)

1,801 g/hour of a 67% strength by weight nitric acid and 71.4 g/hour of chlorobenzene, which has been used for stirring (F) with stream 7, (molar ratio of nitric acid to the aromatic compound 30.2 : 1) are reacted continuously at 90° C and with a residence time of 25 minutes in a three-stage stirred kettle cascade. The reaction mixture is then cooled and separated, at 30° C, by continuous filtration (C 1) into an inorganic phase (stream 4) and an organic phase (stream 5).

Part (stream 6, about 1,179 g/hour) of the inorganic phase (stream 5) is recycled direct to the nitration reactor and the other part (stream 7) is extracted (F) with the chlorobenzene (stream 1). After phase separation (C2), the chlorobenzene phase (stream 27) which is charged with nitrochlorobenzene is fed to the reactor (A) and the inorganic phase (stream 20) is fed continuously to a column (D) which is operated under 760 mm Hg and at a temperature at the top of about 100° C.

The nitric acid-free stream of water taken off over the top of the column is withdrawn from the system after the organic constituents (about 1.8 g/hour) which have also distilled over the top have been separated off (C3) (amount withdrawn from the system about 17 ml of water per hour; stream 10).

The sump discharge from the column (about 580 g/hour of 67% strength by weight nitric acid) is fed, together with 80 g/hour of a 98% strength by weight fresh nitric acid, to the nitration reactor. Together with the directly recycled part of the inorganic phase, these two streams provide the nitric acid feed, described initially, for the nitration.

After washing with water (E), the organic phase is twice treated with one and a half times the amount of 2% strength by weight sodium carbonate solution and freed, by rectification in a column, from unconverted starting material and water, which are taken off over the top.

Yield: 99.5 g/hour of nitrochlorobenzene of the following composition (% by weight):
o-nitrochlorobenzene; 36.6
m-nitrochlorobenzene; 0.9
p-nitrochlorobenzene; 62.5
corresponding to a theoretical yield of 99.5% of nitrochlorobenzene.

EXAMPLE 13

(Route of the material streams: compare FIG. 7)

515 g/hour of a 66% strength by weight nitric acid and 68.5 g/hour of toluene (molar ratio of nitric acid to the aromatic compound 7.3 : 1) are reacted continuously at 70° C and with a residence time of 25 minutes in a cascade of three loop reactors. The reaction mixture is then cooled and continuously separated, at 30° C, into an inorganic phase and an organic phase in a separator (C1).

Part (stream 6) (about 307 g/hour) of the inorganic phase is recycled direct to the nitration reactor and the other part (stream 7) (about 162 g/hour) is fed, together with the wash water from the organic phase (about 36.5 g/hour), to a column (D) which is operated under 760 mm Hg and at a temperature at the top of about 100° C.

The nitric acid-free stream taken off over the top of the column is divided into two parts after separating off the nitrotoluene (about 3 g/hour) which has distilled over together with the water and one part is used for washing (E1) the organic phase (stream 19, 20 g/hour) and the other part (stream 10, about 14 g of water/hour) is withdrawn from the system.

The sump discharge from column (D) (stream 12, about 162 g/hour of 66% strength by weight nitric acid) is fed, together with 51.2 g/hour of a 98% strength by weight fresh nitric acid (stream 13), to the nitration reactor.

The washed organic phase (stream 22) is washed (E2) with dilute sodium hydroxide solution in order entirely to remove any cresols, which may be present in traces, and residual nitric acid and is freed from unconverted starting material and water in a top column (G) at a sump temperature of about 170° C/25 mm Hg. The product composition and yield are as in Example 2.

EXAMPLE 14

(Route of the material streams: compare block diagram 7, partial stream 6 = zero)

The nitration and the separation into an organic phase and an inorganic phase are carried out as described in Example 13. The organic phase is then washed, and worked up, as described in Example 13. The inorganic phase (stream 5 = stream 7; about 468.1 g/hour) is fed to column (D) which is operated under 760 mm Hg and at a temperature at the top of about 100° C.

A 62.7% strength by weight nitric acid (stream 12, about 464 g/hour) is taken off as the sump discharge and a mixture of about 33.5 g/hour of water and 7 g/hour of organic product (mainly nitrotoluene) is taken off over the top.

The subsequent flow routes and working up are as described in Example 13.

Yield: as described in Example 2.

What is claimed is:

1. Process for the preparation of mononitro-aromatic compounds which comprises (1) reacting a reactive aromatic compound with 40 to 68% strength by weight nitric acid in the absence of sulphuric acid, until mononitration is essentially complete (2) separating mechanically said nitration reaction mixture into an organic phase and an inorganic phase, (3) washing of the organic phase first of all with water and then with dilute alkali solution and subsequent separation of the unconverted starting material and of the adhering water by means of rectification (4) feeding said inorganic phase and, if necessary, the wash water of the first water wash of the organic phase, to a rectification column in which (a) water is withdrawn over the top and (b) a fraction which has a higher nitric acid content than the feed is taken off from the sump, (5) recycling said material withdrawn from the sump to the nitration reaction vessel with the addition of fresh concentrated nitric acid and (6) withdrawing from the system an amount of the top product from said column which corresponds to the water of reaction and that which enters with the nitric acid that is added.

2. Process of claim 1 wherein the nitration reaction mixture is diluted with water or dilute nitric acid before separation into an organic phase and an inorganic phase.

3. Process of claim 1 wherein the temperature of the nitration reaction mixture is lowered before separation into an organic and an inorganic phase.

4. Process of claim 1 wherein a fraction of the inorganic phase which has a lower nitric acid content than the feed is withdrawn from a sidestream take-off in the rectifying section of the column.

5. Process of claim 1 wherein the amount of inorganic phase fed to the column is at least that which corresponds to the water of reaction formed during the nitration.

6. Process of claim 1 wherein the nitric acid-containing wash water from the wash of the organic phase is added to that part of the inorganic phase which is to be fed to the column and the organic phase, which then separates from the inorganic phase, is separated off by mechanical means.

7. Process of claim 1 wherein the organic constituent dissolved in the inorganic phase is distilled over the top during the rectification and is then separated off.

8. Process of claim 1 wherein the inorganic phase which passes to the rectification is previously extracted with the aromatic compound to be nitrated.

9. Process of claim 1 wherein the nitration is carried out at 30° to 120° C.

10. Process of claim 6 wherein the nitration is carried out at 50° to 90° C.

11. Process of claim 1 wherein the nitration is carried out in excess aqueous nitric acid at concentrations of 40 to 68% by weight nitric acid and with molar ratios of nitric acid to the aromatic compound of 4 : 1 to 50 : 1.

12. Process of claim 8 wherein the nitration is carried out in excess aqueous nitric acid at concentrations of 40 to 68% by weight of nitric acid and with molar ratios of nitric acid to the aromatic compound of 7 : 1 to 30 : 1.

13. Process of claim 1 wherein the reactive aromatic compounds are mononuclear or polynuclear hydrocarbons which are unsubstituted or substituted by alkyl, cycloalkyl, alkoxy, hydroxyl, acylated amino, halogen or a combination of said substituents.

14. Process of claim 13, wherein the reactive aromatic compounds are benzene, toluene, naphthalene, triisopropylbenzene, ethylbenzene, chlorobenzene, 1,3-xylene, 1,4-xylene and 1,2-xylene.

15. Process of claim 1 wherein the nitric acid employed for the nitration contains dissolved nitrous gases or nitrous acid.

16. Process of claim 1 wherein the nitration, the phase separation and the rectification are carried out continuously.

* * * * *